(12) United States Patent
Sergoyan et al.

(10) Patent No.: US 7,135,869 B2
(45) Date of Patent: Nov. 14, 2006

(54) THICKNESS MEASURING SYSTEMS AND METHODS USING A CAVITY RESONATOR

(75) Inventors: Edward G. Sergoyan, Mill Creek, WA (US); Corbin Champion, Meridian, ID (US); Robert G. Olsen, Pullman, WA (US)

(73) Assignee: The Boeing Company, Chicago, IL (US)

( * ) Notice: Subject to any disclaimer, the term of this patent is extended or adjusted under 35 U.S.C. 154(b) by 67 days.

(21) Appl. No.: 10/759,246

(22) Filed: Jan. 20, 2004

(65) Prior Publication Data

US 2005/0156606 A1    Jul. 21, 2005

(51) Int. Cl.
*G01R 27/04*    (2006.01)
(52) U.S. Cl. .................. 324/636; 324/635; 324/644
(58) Field of Classification Search ............... 324/635, 324/636, 644, 229
See application file for complete search history.

(56) References Cited

U.S. PATENT DOCUMENTS

| | | | | |
|---|---|---|---|---|
| 5,491,422 A | * | 2/1996 | Bitar et al. ................ | 324/636 |
| 5,500,599 A | * | 3/1996 | Stange ....................... | 324/634 |
| 5,563,505 A | * | 10/1996 | Dorothy et al. ............. | 324/71.6 |
| 5,648,038 A | * | 7/1997 | Fathi et al. ................. | 264/406 |
| 6,184,694 B1 | * | 2/2001 | Anderson et al. ........... | 324/635 |
| 6,297,648 B1 | * | 10/2001 | Lunden ...................... | 324/635 |
| 6,359,446 B1 | * | 3/2002 | Little, Jr. .................... | 324/637 |
| 6,989,675 B1 | * | 1/2006 | Kesil et al. ................. | 324/636 |

OTHER PUBLICATIONS

Laplante, Phil; Electrical Engineering Dictionary; CRC Press LLC, 2000; p. 721.*
Tina Hilding, et al., "WSU Students Come Up With Potential Solutions to Boeing's Sticky Problem", Jun. 19, 2002, whole document.
Corbin Champion, et al. "Measuring Paint Thickness on Composite Materials", Apr. 30, 2002, pp. 1-8.

* cited by examiner

*Primary Examiner*—Diane Lee
*Assistant Examiner*—Marina Kramskaya
(74) *Attorney, Agent, or Firm*—Baker & Hostetler LLP

(57) ABSTRACT

Film thickness measurement systems and methods are provided that utilize a signal generator having a Gunnplexer design and a resonant frequency detector to correlate the shift in resonant frequency experienced by a resonant cavity having one face abutting a test object. The shift is resonant frequency is determinative of a linear or near linear correlation between film thickness and the resonant frequency shift.

23 Claims, 9 Drawing Sheets

THICKNESS MEASURING SYSTEMS AND METHODS USING A CAVITY RESONATOR

FIELD OF THE INVENTION

The present invention relates generally to the field of measurements. More particularly, the present invention relates to non-destructively measuring the thickness of a film using electromagnetic cavity resonance principles.

BACKGROUND OF THE INVENTION

Non-destructive measurement of a film thickness is an important objective for many industries. For example, in the aircraft industry paint for functional and decorative purposes is often applied to control surfaces which may have near critical weight. Also, prior to applying a surface paint, care must be taken to make sure that an adequate amount of primer is applied. To act as a proper corrosion inhibitor the primer must typically be applied uniformly to a desired thickness. For example, in some aircraft applications, a desired thickness is between 0.4 and 1.0 mils (thousandths of an inch) to the surface of the substrate. Moreover, depending on the model of aircraft over 500 pounds of primer paint may be applied to each aircraft according to customer specifications. Since the weight and distribution of paint on control surfaces may sometimes affect the performance of the aircraft it is desirable to apply and measure the paint in a controlled means and generally to keep the thickness to a minimum. This measurement is desirable to insure that the primer is sufficiently thick for corrosion protection, but not so thick as to unnecessarily add to the weight of the airplane and affect fuel efficiency. After the primer thickness is determined to be of sufficient thickness, a top coat can be applied.

Control surface components that are made of a metallic material can have their coatings measured by several conventional commercial tools. However, increasingly more components are now manufactured from composite materials such as carbon fiber epoxy or fiberglass. These materials are difficult to measure using conventional techniques since they are only semi-conductive at best.

Another conventional alternative is to wait for the paint to dry and measure thickness indirectly by weighing the component in question. This can result in an undesirable cycle delay of, for example, up to three hours. When primer needs to be measured on a composite component, the component is first weighed and then painted. Since no direct measurement technology is available for composite materials, when the primer is suspected of being too thick or uneven, the component typically must be disassembled and repainted at significant cost and risk of damage.

Commercial ultrasonic measurement systems, such as Panametric 45L Deluxe®, are available which give some paint measurement thickness data for some types of composites. The Panametric 45L Deluxe® is useable for relatively thick coatings, but for thin coatings of paint this ultrasonic system is not sufficiently reliable to meet usual aircraft specification requirements.

Additionally, the non-destructive measurement of film thickness is of concern to other industries such as both the automotive industry and the paper production industry. In the automotive industry, the analysis of the primer paint thickness is important, for example, to determine whether additional touchup work is required for some of the exotic paint applications common to the industry. In the paper industry, maintaining a check on the uniformity of the paper with a sensor can be an important quality control issue. In both these industries, and with the increasing use of composite materials, it has become apparent that current methods of measurement that work on metallics or thick films but not on semi-conductive materials or thin films are not sufficient.

Therefore, there is a need in various industries for systems and methods that are capable of non-destructively measuring the thickness of thin film materials and verify that the thickness is within specifications.

SUMMARY OF THE INVENTION

The foregoing needs are met, to a great extent, by the present invention, wherein in some embodiments systems and methods are provided that are capable of non-destructively measuring the thickness of thin film materials and/or verifying that the thickness is within specifications.

In accordance with one embodiment of the present invention, a thickness measurement system is provided, comprising an electromagnetic cavity resonator having an exposed side, a signal decoupler coupled to the cavity resonator, an signal amplitude detector coupled to the decoupler, a frequency signal generator coupled to the processing unit and to the decoupler, and a processing unit coupled to the amplitude detector that processes, a correlating algorithm correlating a resonant frequency shift detected by the amplitude detector to a surface thickness of a sample being measured.

In accordance with another embodiment of the present invention, a thickness measurement system is provided, comprising a resonating means for resonating an electromagnetic signal, having an exposed side, a decoupler means for decoupling signals from the resonating means, and connected to the resonating means, an signal detecting means for detecting an amplitude of signals from the decoupler means, and connected to the decoupler means, a frequency signal generating means for generating frequency signals, coupled to the processing means and the decoupler means, and a processing means for processing, coupled to the signal detecting means, or having correlating means for correlating means for correlating a resonant frequency shift detected by the detecting means to a surface thickness of a sample being measured.

In accordance with yet another embodiment of the present invention, a method for thickness measurement is provided, comprising the steps of abutting an open faced electromagnetic cavity resonator to a sample having a film thickness, sweeping frequencies in the cavity resonator using a signal generator having a Gunnplexer, detecting a resonant frequency of the cavity resonator using a reflected energy detector, and determining the thickness of the film from a correlation of a shift of the resonant frequency.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
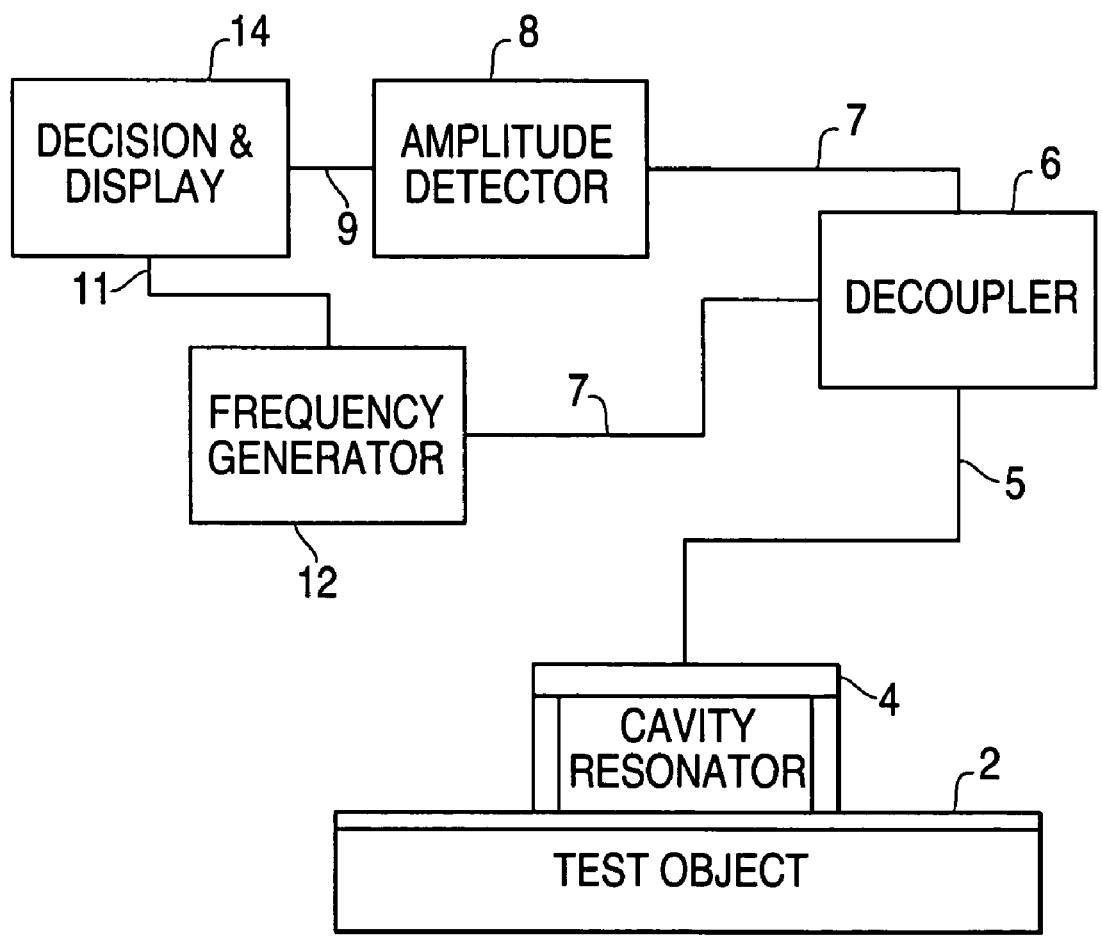
FIG. 1 is a block diagram of an exemplary measuring system according to an embodiment of the invention.

The present invention provides embodiments that result in a portable and accurate system, that will also work for poorly conductive substrates. The invention will now be described with reference to the drawing figures, in which like reference numerals refer to like parts throughout.

FIG. 1 is a block diagram of an exemplary measuring system 10. The exemplary measuring system 10 is shown with a test object 2 in proximity to an exemplary cavity resonator 4. The cavity resonator 4 has an exposed face and is connected via a line 5 to a decoupler 6. The decoupler 6, in turn, is connected to an amplitude meter 8 and a frequency generator 12 via lines 7. The amplitude meter 8 is connected to a decision and display unit 14 via line 9. The frequency generator 12 is also connected to the decision and display unit 14 via line 11.

In operation, the cavity resonator 4 is affixed to the sample or test object 2 with the exposed face abutting the test object 2. That is, the surface of the test object 2 operates to form a "wall" of the cavity resonator 4 and thereby form a complete electrical circuit. The frequency generator 12 is engaged to provide a signal input at many different frequencies which passes through the decoupler 6 and into the cavity resonator 4. When the signal input arrives at the cavity resonator 4, part of the signal is reflected and travels back into the decoupler 6, which passes it on to the amplitude meter 8. The amplitude meter 8 takes the reflected wave and reports an amplitude to the decision and display unit 14. The decision and display unit 14 also receives the frequencies used from the frequency generator 12. The frequency of the input that provided the smallest reflected wave is evaluated based on Eq. (3) (provided below) to determine the thickness of the paint or surface material on the test object 2.

When the amplitude meter 8 registers a minimum real power (i.e., power is absorbed by the system), resonance of the cavity resonator 4 has been obtained and the resonant frequency is resolved. The decision and display unit 14 then correlates the shift in frequency to arrive at the corresponding thickness and displays this thickness for the user to read or to an external device, for example, a controller such as a PC. In the exemplary embodiment 10, the decision and display unit 11 is performed by a Hewlett-Packard 8510 network analyzer. The frequencies generated by the exemplary frequency generator 12 is preferably provided by a Gunnplexer.

Figure 2:
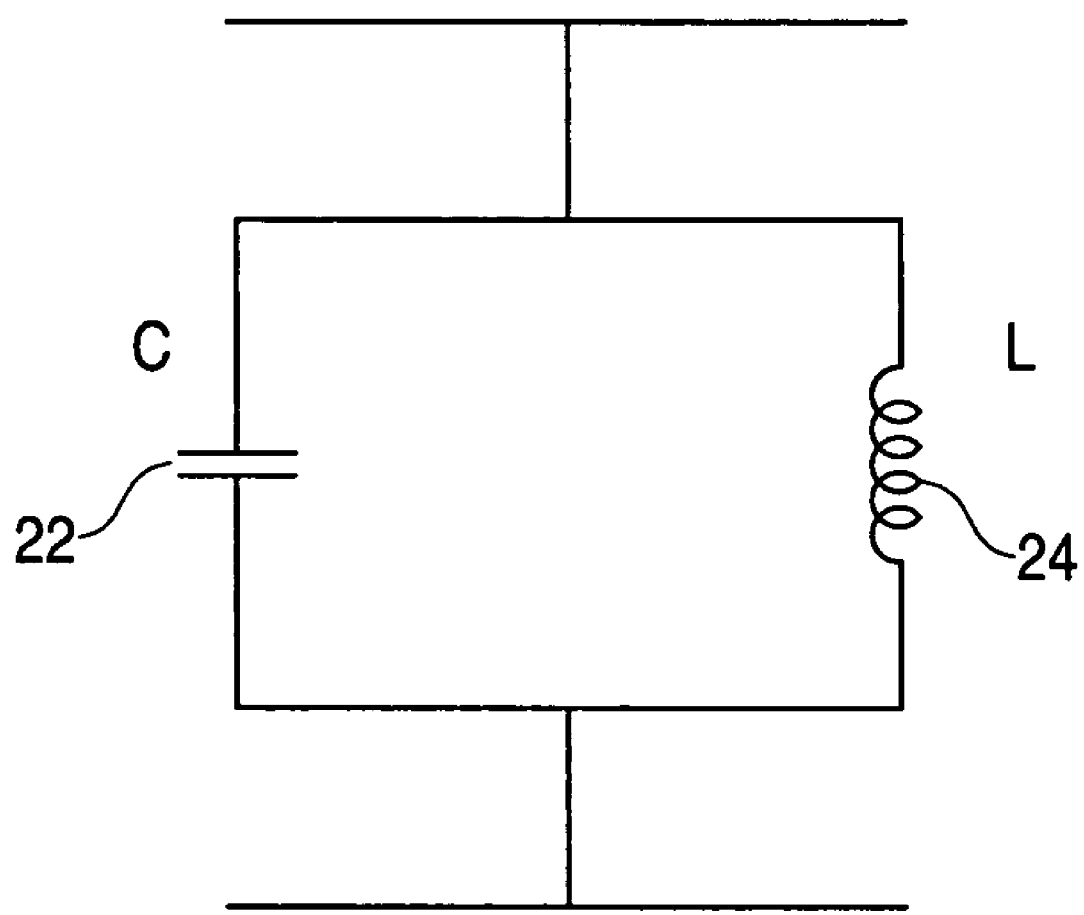
FIG. 2 is a circuit diagram of a resonant circuit.

FIG. 2–5 illustrate some principles of circuits as used in some embodiments of the invention, FIG. 2 is a diagram of a resonant circuit 20 is shown having a capacitive element 22 in parallel with an inductive element 24. From circuit theory it is known that the impedance $Z_C$ of the capacitor 22 and $Z_L$ of the inductor 24 are a function of frequency:

$$Z_C = \frac{1}{j\omega C}, \qquad \text{Eq. 1}$$

$$Z_L = j\omega L, \qquad \text{Eq. 2}$$

where C is the capacitance of the capacitor 22, L is the inductance of the inductor 24, j is an imaginary number, and $\omega$ is the radian frequency. At any specified input signal frequency f, the power in the circuit 20 can be complex S, having an imaginary component Q and a real component P, which can be represented by a power angle diagram.

Figure 3:
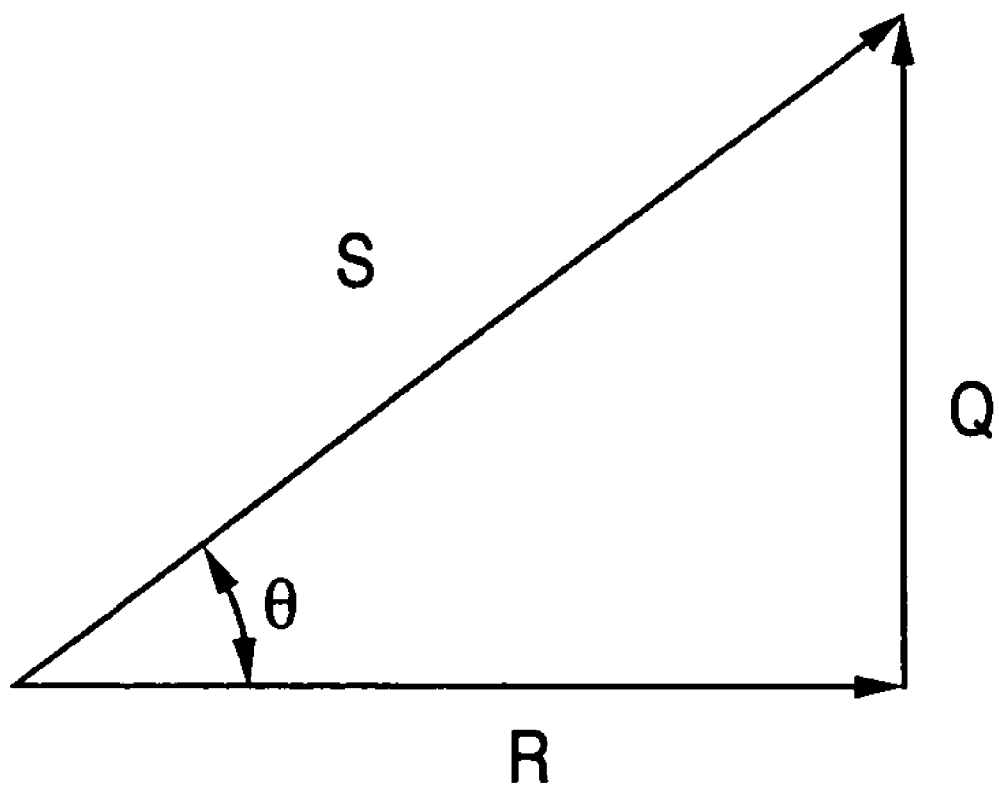
FIG. 3 is a power angle diagram.

FIG. 3 illustrates a power angle diagram 30. The power vector 8 can have a positive angle $\theta$ or a negative angle $-\theta$, depending on the value of the imaginary power component Q. If Q is positive, then the circuit 20 is predominately inductive. If Q is negative, then the circuit 20 is predominately capacitive. For illustrative purposes only the diagram 30 shows the circuit 20 as being inductive.

Figure 4:
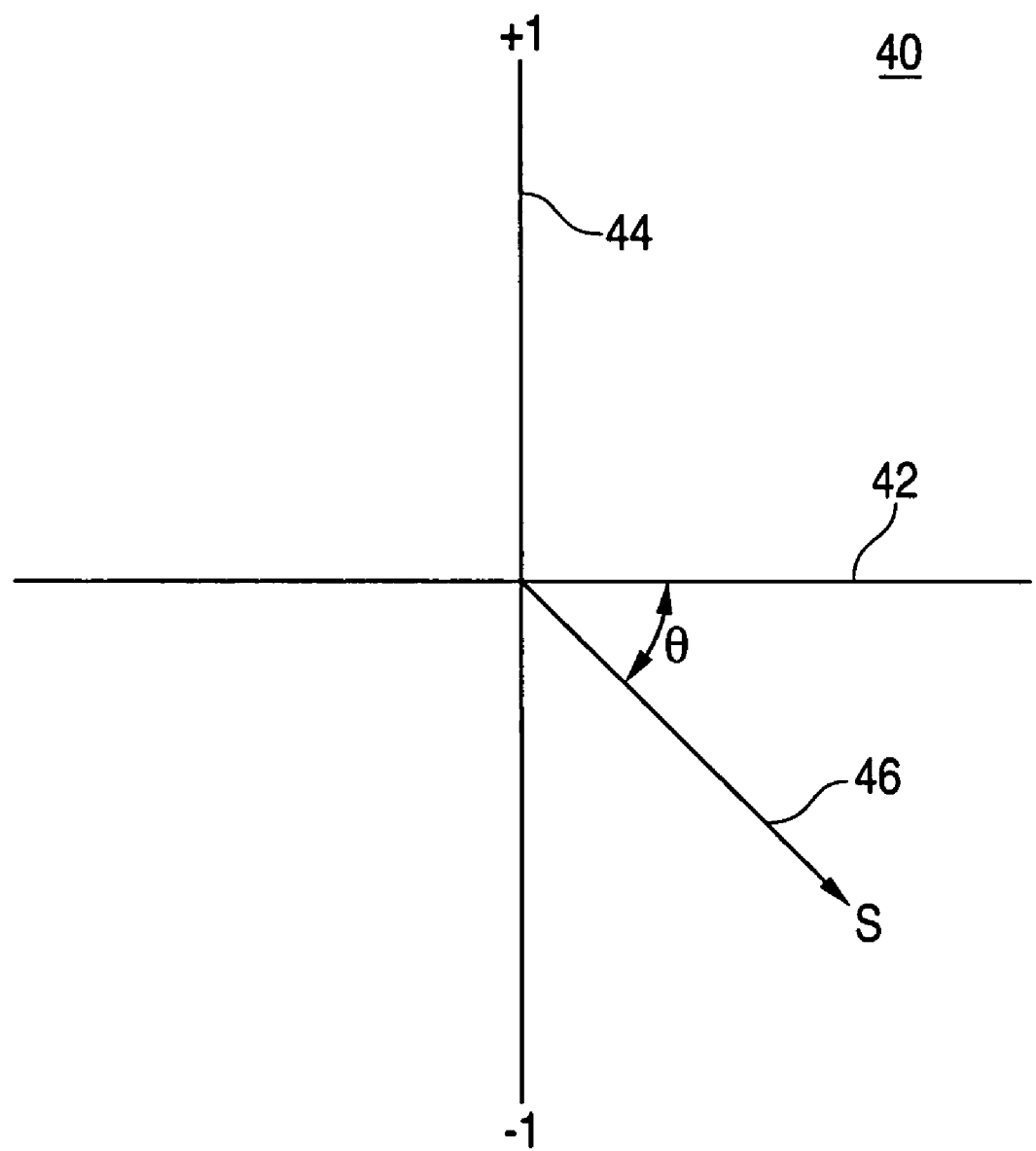
FIG. 4 is a power vector diagram in a real-imaginary plane.

FIG. 4 is an illustration of the power vector S in a real-imaginary plane 40. The "x-axis" 42 of the real-imaginary plane 40 represents a purely resistive power—equivalent to P in the diagram 30 of FIG. 3. The "y-axis" 44 represents a purely reactive power—equivalent to Q in the diagram 30 of FIG. 3. Here, the power vector S 46 is shown to have a negative angle $\theta$ 48. Therefore, in this instance the power vector S 46 connotes a capacitive circuit.

When a circuit with reactive elements is either capacitive or inductive, there will be a non-zero angle $\theta$. However, when $\theta$ is zero, only real power (shown on the x-axis as P) will be consumed by the circuit. When a circuit has both inductive and capacitive elements, the situation where $\theta$=zero can only occur when the circuit is in resonance $$\left(\text{i.e., } \frac{1}{j\omega C} = j\omega L\right).$$

This, of course, occurs when the frequency f is such that the two terms above cancel out. For known values of L and C, the resonant frequency is determinable as:

$$f_o = \frac{1}{2\pi}\sqrt{\frac{L}{C}} \qquad \text{Eq. 3}$$

Therefore, for a given circuit, the resonant frequency $f_o$ is a fixed value. If a circuit, such as shown in FIG. 2, is modified with an incremental inductance ΔL and incremental capacitance ΔC, then Eq. 3 will be affected accordingly, and the resonant frequency $f_o$ will shift.

Figure 5:
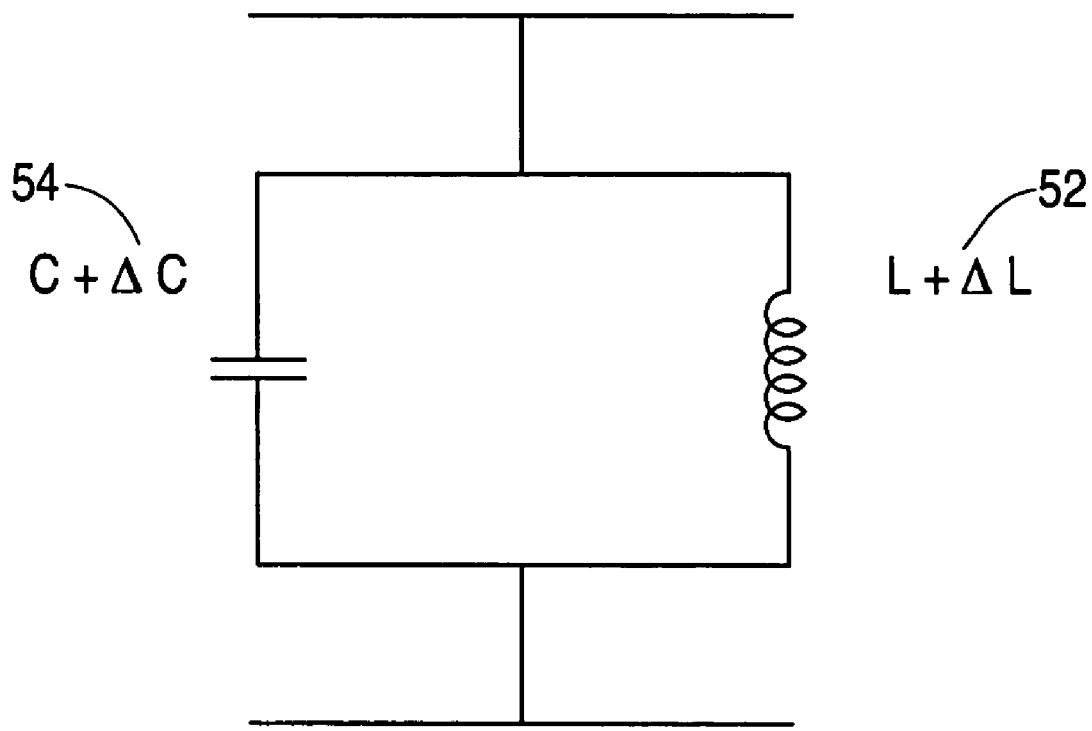
FIG. 5 is a circuit diagram of a modified resonant circuit.

FIG. 5 is an illustration of a circuit 50 having incremental ΔL 52 and Δ C 54 added to the system of FIG. 2. It is apparent that there is a proportional relationship between the shift in resonant frequency $f_o$ and the incremental impedances added to the system. An exploitation of this relationship is devised herein to correlate a thickness of a known material with the resulting effect on the resonance of a resonating cavity system. In particular, if one face of a resonating cavity is replaced with a material that alters the impedance of the resonating cavity, the natural or resonant frequency of the resonating cavity will shift. By correlating the amount of the shift in frequency with the thickness of the material, a thickness measuring system can be devised. The principles of resonating cavities are well known and can be found in such treatises such as "Foundations for Microwave Engineering" by R. E. Collin, McGraw-Hill Inc., 1966.

Figure 6:
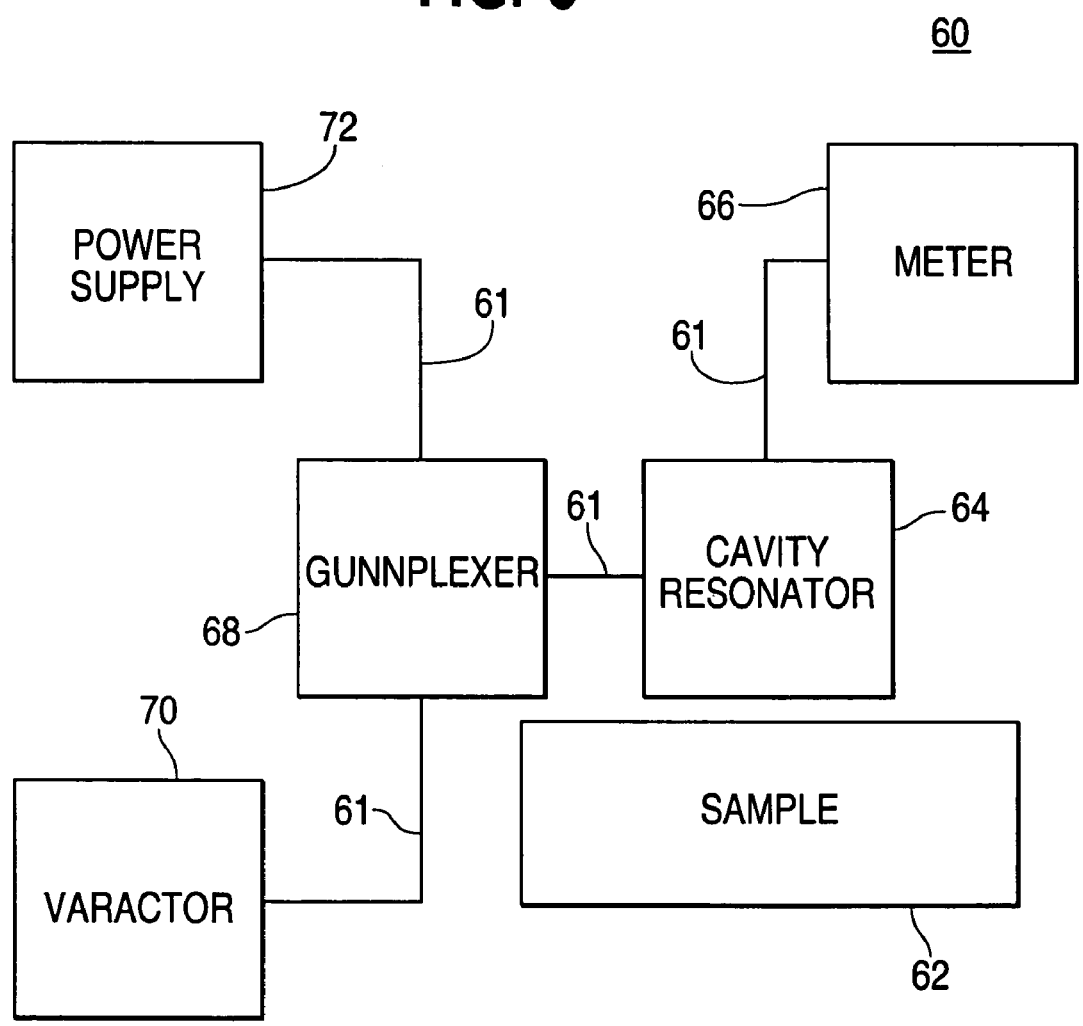
FIG. 6 is an illustration of another exemplary measuring system.

FIG. 6 is a block diagram of another exemplary measurement system 60. The exemplary system 60 is similar to the system 10 of FIG. 1, but is implemented in a slightly different manner. The exemplary system 60 contains a cavity resonator 64 connected to a power meter 66 via a signal line 61. The cavity resonator 64 is also connected to a frequency generating Gunnplexer 68 via a signal line 61. The Gunnplexer 68 is powered by a DC power supply 72 and controlled by a DC varactor 70, via lines 61.

In operation, the Gunnplexer 68 is energized by the power supply 72 and is frequency controlled by a DC voltage supplied via the varactor 70 to the voltage sensitive frequency (e.g. VCO) input of the Gunnplexer 68. As the input voltage is varied, the Gunnplexer's output frequency will vary. The varied output frequency is channeled to the cavity resonator 64 and the power dissipated by the cavity resonator 64 is detected by the power meter 66. Based on the power meter's 66 response, the user can adjust the varactor 70 to arrive at the resonant frequency.

A preferred Gunnplexer 68 in the exemplary embodiments of FIGS. 1 and 6 is made by AR2 Communications Products and has a frequency modulated transceiver that incorporates an oscillator and Schottky mixer diodes. The Gunnplexer is sometimes called a Gunn oscillator or Gunn diode and is preferably capable of operating in the 10 GHz and higher radio frequency band.

In the exemplary embodiments of FIGS. 1 and 6, the Gunn diode 68 is configured to directly convert DC to RF energy at a preset of 10.680 GHz. It should be appreciated that Gunn diodes can be preset to other frequencies and other power setting as well, according to design preferences. Since the Gunn diode is sensitive to temperature changes, a temperature regulator or heater may be implemented to regulate the Gunn diode.

A tuning varactor 70 is mounted close to the Gunn diode which will deviate or vary the fundamental frequency by typically 60 MHz when an appropriate tuning voltage is applied. When the oscillations are in resonance in the cavity resonator 64, an increase in real voltage in the resonant system is generated that can be related to the material or paint thickness because the "front wall" of the cavity resonator 64 is the test object 2 having the material or paint thickness. The operator, or by decision from the decision and display unit 14, can tune to the resonant frequency of the test object 2, much like tuning a radio to the best signal for a favorite radio station.

Due to the use of a Gunn diode, the exemplary measurement systems 10 and 60 provides a more reliable measurement value than prior art systems. Specifically, the relative amplitude output of the cavity resonator 4 or 64 is used to determine which of the frequencies input into the cavity resonator 4 or 64 corresponds to the resonant frequency $f_0$ rather than an absolute amplitude. Since the absolute amplitude of the output is not relied upon, no assumptions are required concerning the amplitude of the oscillator output. That is, stability to an absolute voltage of the oscillator is not necessary. Therefore, the oscillator amplitude may drift with time without affecting the measurement. This provides an additional degree of freedom over prior art systems.

Also, by using a Gunnplexer or Gunn diode as a signal source, a smaller packaging of the exemplary systems can be accomplished, since a typical frequency generator is not needed. Another advantage over contemporary systems is that there is no "reference voltage" required for the Gunnplexer and since a variable frequency discrimination is used, a greater versatility can be achieved.

Based on the system 10 and 60 of FIGS. 1 and 6, respectively, several samples of composite materials were tested for film thickness determination. These samples had varying thickness of paint and were measured with a precision height gauge to determine paint thickness at discrete areas on the samples. Each sample contained a base spot where the paint is removed to a predetermined level to establish a reference surface thickness. The samples were then tested using the exemplary systems, wherein data was read and recorded for each sample using a minimum value of 11 reflections using an HP85 10 network analyzer.

Figure 7:
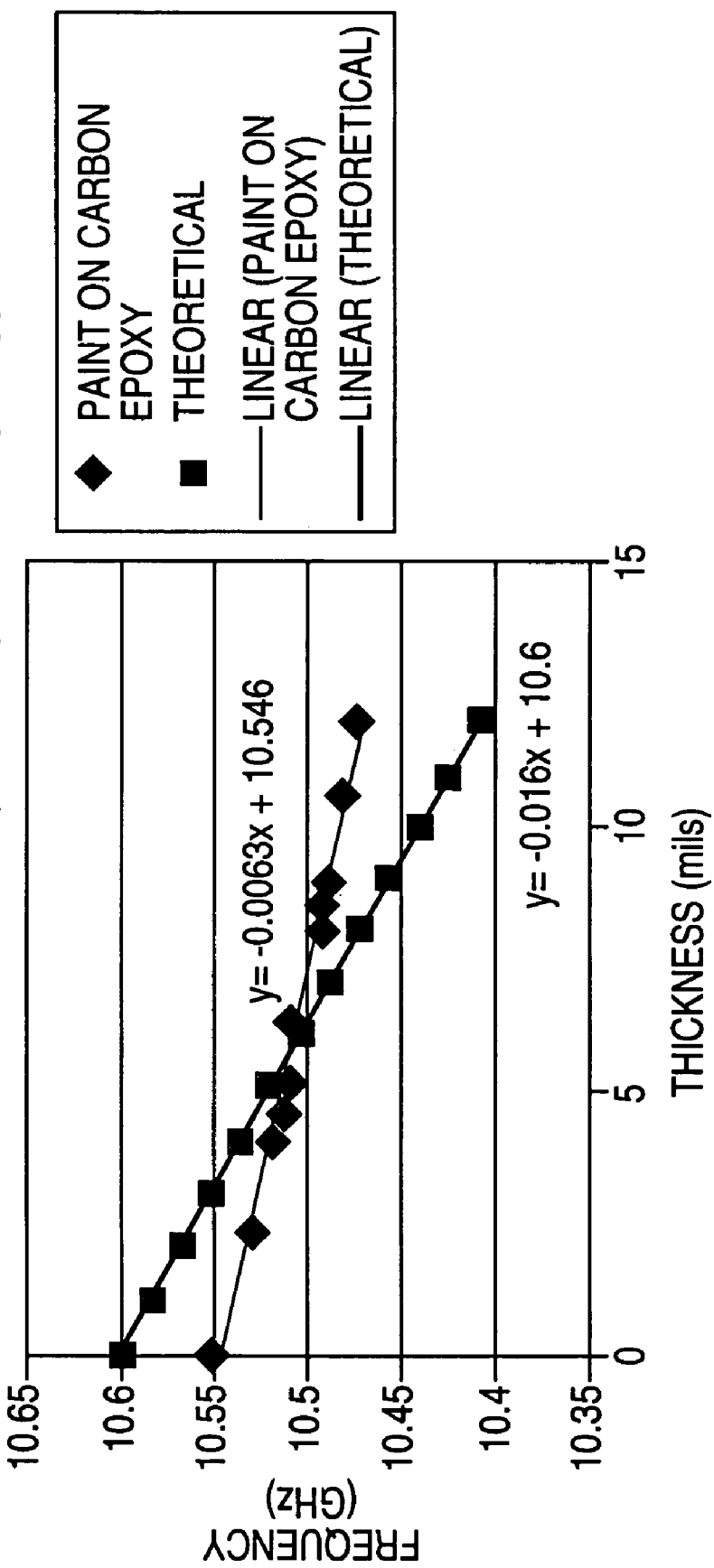
FIG. 7 is a graph illustrating an exemplary resonance frequency versus thickness response.
Figure 8:
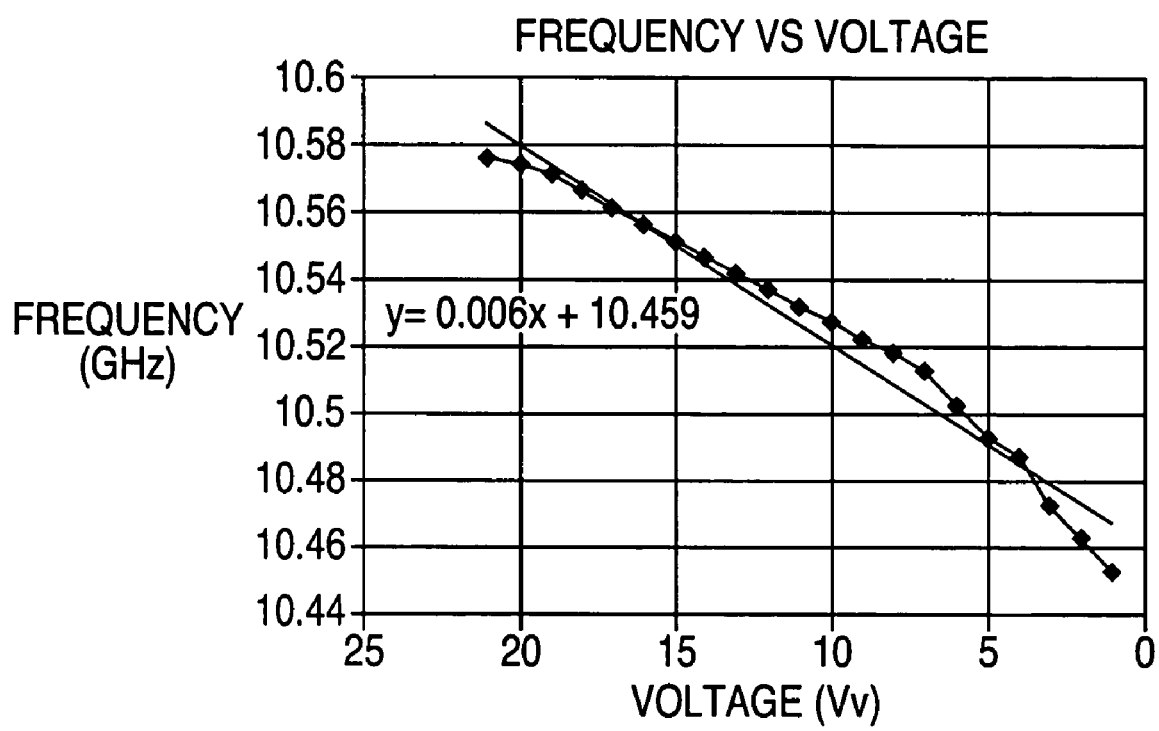
FIG. 8 is a graph illustrating an exemplary resonance frequency versus drive voltage response.

FIGS. 7 and 8 are an exemplary charts 70 and 80, respectively, showing the measured frequency response for the samples discussed above as compared to theoretical predictions. From FIG. 7, it is apparent that the thickness of the samples and the frequency response are substantially linearly related. Specifically, in FIG. 7 the diamond annotated theoretical line (paint or carbon epoxy) has a slope of approximately 0.0063 and a y-intercept of approximately 10.546 GHz. The square annotated measured response line has a slope of approximately −0.016 and a y-intercept of approximately 10.6 GHz. It should be noted here, that the linear relationship of the measured data compares very favorably with the theoretical data. Accordingly, the linear relationship appears to demonstrate an approximate 6.3 MHz change per mil of paint thickness.

In FIG. 8, a comparison of the frequency shift and the drive voltage shows a near identical relationship as seen in FIG. 7, having an approximate shift of 6 MHz per drive voltage. Therefore, based on the results shown in FIGS. 7 and 8, it can be expected that with minor adjustment to the theoretical model, an accurate measurement of less than 0.5 thousandths of an inch of thickness can be obtained in practice for some paint thickness.

Figure 9:
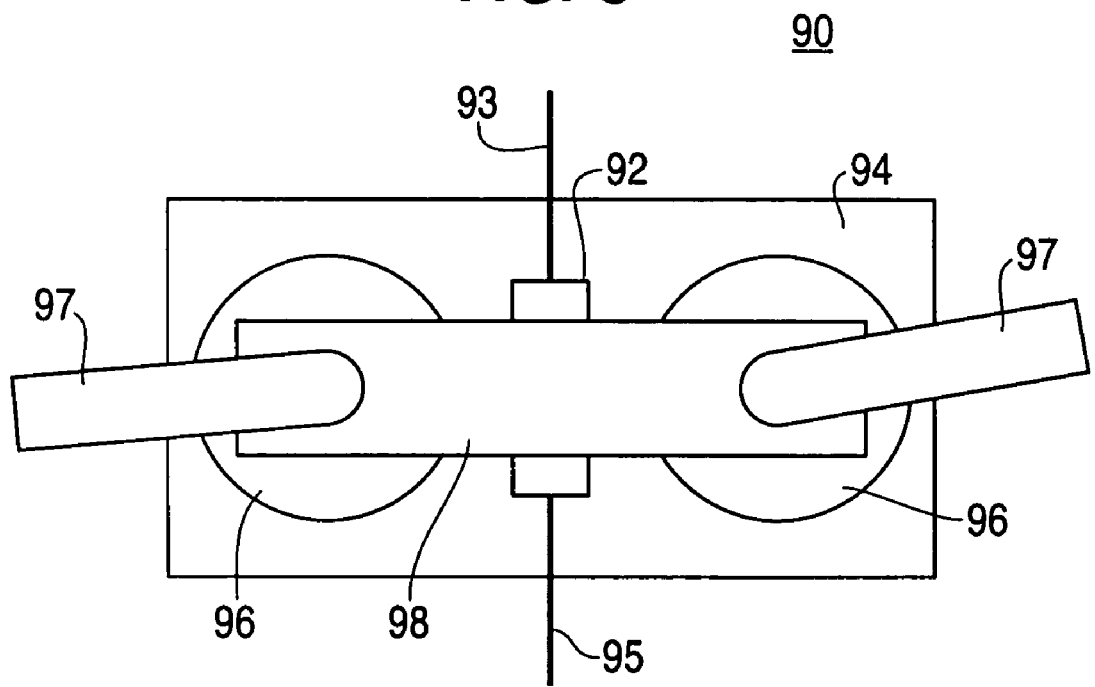
FIG. 9 is an illustration of an exemplary cavity resonator apparatus.

FIG. 9 is an illustration of an exemplary cavity resonator apparatus 90. The exemplary apparatus 90 has a three chamber cavity resonator 92 of a Filtek design. The cavity resonator 92 is fed a frequency signal via input cable 93 and the power is output by cable 95. The cavity resonator 92 is secured to the sample 94 via two suction assemblies 96 that flank the cavity resonator 92. Suction tubes 97 are shown attached to the suction assemblies 96. The cavity resonator 92 and the suction assemblies 96 are supported via a plate 98 (shown here as a plexiglass sheet). The suction tubes 97 are connected to a suction-generating device (not shown) which, when engaged, generate a suction in the suction assemblies 96 and press the cavity resonator 92 uniformly and with a constant pressure upon the sample 94.

The exemplary cavity resonator 92 is of three chamber design which results in a narrower resonance response than conventional systems and, hence, a more accurate measurement. Therefore, by narrowing the critical resonance and providing a more stable frequency response, a more accurate measurement can be required. Of course, by design preference, more or less resonating chambers may be implemented.

Additional refinements can be made to the attachment apparatus 90, such as, for example, implementing a signal switch about the input section of the resonator 92 or a bypass filter. Also, while FIG. 9 illustrates two suction assemblies 96 more, or even less, suction assemblies 96 may be utilized, as desired. For example, one can easily modify the current design to have the cavity resonator 92 centered within a single and "larger" suction assembly 86 to facilitate a "one-piece" type design.

Due to the ability to measure film thickness or composite materials, embodiments of this invention may be used to study film on carbon fiber honeycomb or fiberglass honeycomb materials that have an electrically conductive layer. For example, advanced helicopter blades are known to be composed of a carbon fiber epoxy with an imbedded copper grid. An additional application of embodiments of this invention can also be in the measurement of the vapor barrier used in the fuel cells.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A thickness measurement system for measuring a film thickness of a sample, comprising:
    an electromagnetic cavity resonator having an exposed side adapted to contact a portion of the surface of the sample;
    a suction assembly to apply a pressure to the cavity resonator to secure the cavity resonator to the measurement sample;
    a signal decoupler coupled to the cavity resonator;
    a signal amplitude detector coupled to the decoupler;
    a processing unit coupled to the amplitude detector that processes;
    a frequency signal generator coupled to the processing unit and to the decoupler; and
    a correlating algorithm correlating a resonant frequency shift detected by the amplitude detector to the film thickness of the portion of the surface of the sample being measured, wherein during the measurement the exposed side of the cavity resonator is pressed against the portion of the surface of the sample.

2. The thickness measurement system of claim 1, wherein the electromagnetic cavity resonator has a plurality of cavities.

3. The thickness measurement system of claim 1, wherein the frequency signal generator is one of a Gunnplexer or a Gunn Diode.

4. The thickness measurement system of claim 1, wherein the amplitude detector detects a voltage.

5. The thickness measurement system of claim 1, wherein the amplitude detector detects a power.

6. The thickness measurement system of claim 1, further comprising a DC supply coupled to the frequency signal generator.

7. The thickness measurement system of claim 1, further comprising a varactor DC supply capable of controlling a frequency generator output frequency.

8. The thickness measurement system of claim 1, wherein the processing unit is a personal computer.

9. The thickness measurement system of claim 1, wherein the cavity resonator is resonant at a natural frequency of approximately 10.6 GHz.

10. A thickness measurement system for measurement of a film thickness of a sample, comprising:
    a resonating means for resonating an electromagnetic signal, having an exposed side adapted to contact a portion of the surface of the sample;
    a decoupler means for decoupling signals from the resonating means, and connected to the resonating means;
    a signal detecting means for detecting an amplitude of signals from the decoupler means, and connected to the decoupler means;
    a processing means for processing, coupled to the signal detecting means;
    a frequency signal generating means for generating frequency signals, coupled to the processing means and the decoupler means;
    correlating means for correlating a resonant frequency shift detected by the detecting means to the film thickness of the portion of the surface of the sample being measured; and
    suction means for applying a pressure to the resonating means to secure the exposed side of the resonating means to the measurement sample.

11. The thickness measurement system of claim 10, wherein the frequency signal generating means utilizes a Gunnplexer to generate frequencies.

12. The thickness measurement system of claim 10, wherein the resonating means has a plurality of cavities.

13. The thickness measurement system of claim 10, wherein the frequency signal generating means has Schottky diodes.

14. The thickness measurement system of claim 12, wherein the Gunnplexer is a Gunn Diode.

15. The thickness measurement system of claim 10, wherein the detecting means detects a voltage.

16. The thickness measurement system of claim 10, wherein the detecting means detects a power.

17. The thickness measurement system of 10, further comprising a DC supply means coupled to the frequency signal generating means.

18. The thickness measurement system of claim 10, wherein the processing means is a personal computer.

19. The thickness measurement system of claim 10, wherein the resonating means is resonant at a natural frequency of approximately 10.6 GHZ.

20. A method for thickness measurement for measuring a film thickness of a sample, comprising the steps of:
    abutting an open faced electromagnetic cavity resonator to a portion of the surface of a sample;
    affixing the cavity resonator to the surface of the sample with a substantially uniform pressure using a suction assembly;
    sweeping frequencies in the cavity resonator using a signal generator having a Gunnplexer;

detecting a resonant frequency of the cavity resonator using a reflected energy detector; and determining the thickness of the film from a correlation of a shift of the resonant frequency.

21. The method of claim 20, wherein the correlation is based on a first order equation.

22. The method of claim 20, wherein the electromagnetic cavity resonator has a plurality of cavities.

23. The method of claim 20, wherein the signal generator is one of a Gunnplexer or a Gunn Diode.

* * * * *